(12) United States Patent
Marshall

(10) Patent No.: US 6,524,284 B1
(45) Date of Patent: Feb. 25, 2003

(54) MEDICAL INJECTION PATCH

(76) Inventor: John M. Marshall, 202 S. Michigan St., South Bend, IN (US) 46601

( * ) Notice: Subject to any disclaimer, the term of this patent is extended or adjusted under 35 U.S.C. 154(b) by 0 days.

(21) Appl. No.: 09/540,173

(22) Filed: Mar. 31, 2000

(51) Int. Cl.$^7$ ................................................. A61M 5/32
(52) U.S. Cl. ..................................... 604/272; 604/180
(58) Field of Search .................................. 604/180, 272

(56) References Cited

U.S. PATENT DOCUMENTS 4,380,234 A * 4/1983 Kamen ........................ 604/180
5,728,071 A * 3/1998 Watson et al. ............... 604/180
5,951,521 A * 9/1999 Mastrototaro et al. ....... 604/180

* cited by examiner

Primary Examiner—Gerald A. Michalsky
(74) Attorney, Agent, or Firm—Baker & Daniels

(57) ABSTRACT

This invention relates to a self adhering patch which is positioned upon the needle of a syringe. When the skin of the patient is pierced with the hypodermic needle the patch comes into contact with the skin, self adhering to the skin. As the needle is withdrawn from the patient, the patch remains upon the skin of the patient and serves as a seal against the expulsion of blood or other body fluids from the injection site.

6 Claims, 1 Drawing Sheet

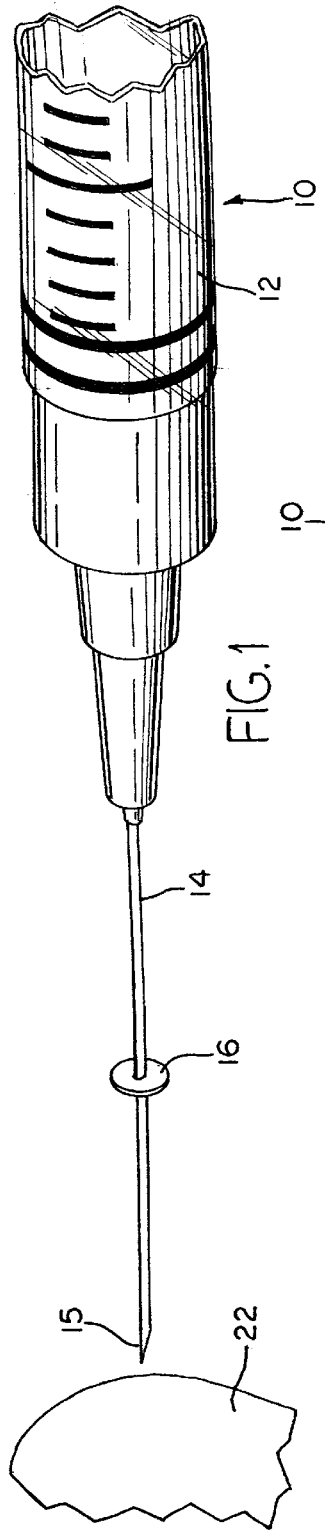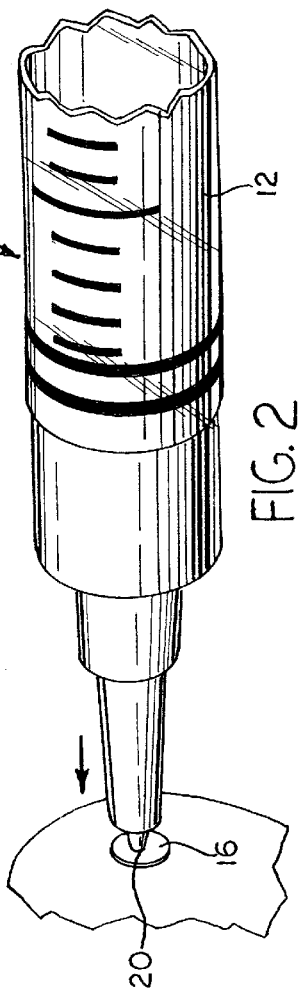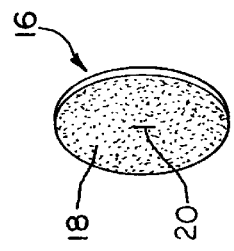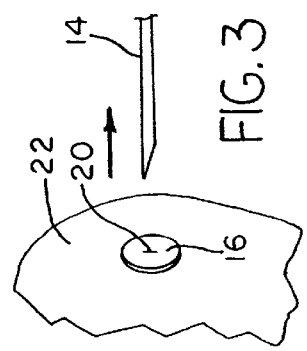

MEDICAL INJECTION PATCH

BACKGROUND OF THE INVENTION

1. Field of the Invention

This invention relates to a self adhering patch which is positioned upon the needle of a syringe. When the skin of the patient is pierced with the hypodermic needle the patch comes into contact with the skin, self adhering to the skin. As the needle is withdrawn from the patient, the patch remains upon the skin of the patient and serves as a seal against the expulsion of blood or other body fluids from the injection site.

2. Discussion of the Prior Art

Much attention is presently being directed to the minimization of the expulsion of a patient's body fluids such as blood when giving shots, drawing blood, or intravenous feeding. Heretofore, patches have been used during the course of blood withdrawal such as shown in U.S. Pat. No. 5,738.641 and for the anchoring and fastening of catheters or hypodermic needles such as shown in U.S. Pat. Nos. 5.236, 421 and 4,838,868.

SUMMARY OF THE INVENTION

This invention relates to a patch for sealing the injection site of a hypodermic needle in the skin of a patient and will have particular application to a patch which is carried by the hypodermic needle.

In this invention the patch is carried by the hypodermic needle which when the needle is inserted into the skin of the patient, the patch adheres itself to the skin over the injection location. When the needle is withdrawn the patch remains upon the skin, serving as a seal.

Accordingly, it is an object of this invention to provide a device for sealing the injection location caused by hypodermic needle in the skin of a patient.

Another object of this invention is to provide a medical injection patch which is carried by a hypodermic needle and which serves to seal the patient's skin about the site of the injection.

Other objects of this invention will become apparent upon a reading( of the following description.

BRIEF DESCRIPTION OF THE DRAWINGS

A preferred embodiment has been chosen for purposes of illustration and description wherein:

FIG. 1 is a perspective view showing a hypodermic syringe in fragmented form carrying the patch of this invention prior to insertion of the hypodermic needle into the skin of the patient.

FIG. 2 is a perspective view showing the hypodermic syringe in fragmented form having its needle inserted into the skin of the patient with the patch adhering to the surface of the patient's skin.

FIG. 3 is a fragmentary perspective view showing the hypodermic syringe being withdrawn from the patient and the patch remaining. sealing the injection site.

FIG. 4 is a perspective view of the patch as seen from the bottom.

DETAILED DESCRIPTION OF THE PREFERRED EMBODIMENT

A hypodermic syringe 10 of standard construction and form is illustrated, having a barrel part 12 and a needle 14 with a pointed end 15 . Within barrel part 12 may be a plunger (not shown) which upon depression serves to force a fluid within the barrel part through needle 14 and into the patient. As stated previously, the hypodermic syringe 10 may be of standard construction and used for injection or withdrawal of fluid.

A patch 16 is provided. Patch 16, shown in FIG. 4 in isolated form, is made of a suitable absorbent material having an adhesive 18 applied to its lower side. Patch 16 may be formed of a self sealing material which closes about the opening 20 through which needle 14 is inserted. Alternatively, the upper side of patch 16 may be provided with a suitable self-sealing membrane with the remainder of the pad being of absorbent material except for the underlying adhesive 18. Prior to use of hypodermic syringe 10. patch 16 is threaded upon needle 14 through the opening 20 formed in the patch. Prior to usage, release paper may be utilized to cover adhesive 18. When the hypodermic is ready for use, any release paper is removed to expose adhesive 18 which faces the pointed end 15 of needle 14. The needle 14 is then inserted into the skin or tissue 92 of the patient as illustrated in FIG. 2 with adhesive side 18 of patch 16 coming in contact with the outer surface of the patient's skin and adhering to the skin After the contents of the barrel part have been injected into the patient, needle 14 is removed as shown in FIG. 3 with patch 16 remaining over the injection site. The sell sealing properties of patch 16 causes opening 20 to close, or at least substantially close preventing blood or other body fluids from seeping from the opening formed in the patient's skin by the hypodermic needle. The absorbent characteristics of the patch serve to collect the expelled body fluid. The patch being sterile serves to protect the injection area until it is safe to remove the patch as the needle opening in the skin heals.

The above invention would have application not only to normal hypodermic syringes used for customary shots but also in the drawing of blood and similar medical procedures where the needle is withdrawn from the patient shortly after insertion. Also, the above invention is not to be limited to the details so explained but rather it may be modified in the course of the amended claims.

What is claimed is:

1. A method of inserting a needle into the skin of a medical patient comprising the steps:

providing a self-sealing patch, impaling said self-sealing patch upon said needle through an opening in said self-sealing patch prior to insertion of said needle, inserting said needle into said skin with said self-sealing patch contacting and adhering to said skin, and withdrawing said needle from said skin with the self-sealing patch remaining upon said skin so that the opening in said self-sealing patch substantially closes and seals said skin at the insertion point of said needle to prevent blood and other bodily fluids from seeping therefrom.

2. In combination, a medical device comprising a needle adapted for insertion into the skin of medical patient and a patch for adherence to said skin about the area of insertion and carried releasably upon said needle prior to and during said insertion, said patch including an absorbent material for absorbing blood and other bodily fluids, and an adhesive for retaining said patch on the skin of patient after said needle is removed, wherein said patch includes an opening through which said needle is inserted, and said opening extends through said absorbent material, said opening through said absorbent material substantial coinciding with the diameter of said needle.

3. The combination of claim 2 wherein said absorbent material is self-sealing so that the opening in said patch is substantially closed upon removal of said needle.

4. The combination of claim 2, wherein said patch includes a self-sealing membrane, and said self-sealing membrane seals the opening in said patch when said needle is removed.

5. In combination, a medical device comprising a needle having a pointed end adapted for insertion into the skin of a medical patient and a self-sealing patch for adherence to said skin about the area of insertion and carried releasably upon said needle prior to and during said insertion, said patch including a layer of absorbent material towards the pointed end of said needle and a self-sealing membrane for inhibiting blood or body fluids from seeping from an opening formed in the patient's skin by said needle after said needle is removed from the patient, wherein said layer of absorbent material extends substantially across the width of the patch.

6. The combination of claim 5, wherein the layer of absorbent material carries an adhesive for adhering the patch to the skin of the patient.

* * * * *